United States Patent
Reid et al.

(10) Patent No.: US 10,288,597 B2
(45) Date of Patent: May 14, 2019

(54) ASSESSMENT METHOD

(71) Applicant: HALOK PTY LTD, West End (AU)

(72) Inventors: Andrew Wilfred Reid, Brisbane (AU); Zuhua Zhang, Toowoomba (AU)

(73) Assignee: Halok Pty Ltd, West End Qld (AU)

( * ) Notice: Subject to any disclaimer, the term of this patent is extended or adjusted under 35 U.S.C. 154(b) by 903 days.

(21) Appl. No.: 14/778,328

(22) PCT Filed: Mar. 20, 2014

(86) PCT No.: PCT/AU2014/000297
§ 371 (c)(1),
(2) Date: Sep. 18, 2015

(87) PCT Pub. No.: WO2014/146173
PCT Pub. Date: Sep. 25, 2014

(65) Prior Publication Data
US 2016/0061806 A1    Mar. 3, 2016

(30) Foreign Application Priority Data

Mar. 20, 2013   (AU) .............................. 2013900977

(51) Int. Cl.
*C04B 7/34*   (2006.01)
*G01N 33/38*   (2006.01)
(Continued)

(52) U.S. Cl.
CPC ......... *G01N 33/383* (2013.01); *C04B 12/005* (2013.01); *C04B 40/0096* (2013.01); (Continued)

(58) Field of Classification Search
USPC .................... 106/638, 692, 697, 700, 705
See application file for complete search history.

(56) References Cited

U.S. PATENT DOCUMENTS 4,028,130 A * 6/1977 Webster ................ C02F 11/008
106/697
5,624,491 A 4/1997 Liskowitz et al.
(Continued)

FOREIGN PATENT DOCUMENTS

| JP | 2001330574 | 11/2001 |
| JP | 2008304446 | 12/2008 |
| JP | 2009121988 | 6/2009 |

OTHER PUBLICATIONS

Written Opinion (issued PCT application from which the U.S. Application is derived). Opinion dated May 9, 2014.
(Continued)

*Primary Examiner* — James E McDonough
(74) *Attorney, Agent, or Firm* — DeLio, Peterson & Curcio, LLC; Kelly M. Nowak

(57) ABSTRACT

The present invention relates, inter alia, to method of assessing the reactivity of a polymerizable material (especially an aluminosilicate) in forming a geopolymer. The present invention also relates to methods of forming a geopolymer, and to geopolymers formed by the method. The method of assessing the reactivity of the polymerizable material may include first assessing whether the polymerizable material is layered or particulate. Next, if the polymerizable material is layered, the method may include measuring the moles of polymerization network forming elements in an amount of polymerizable material, whereby the moles of polymerization network forming elements is indicative of the reactivity of the polymerizable material in forming a geopolymer. Alternatively, if the polymerizable material is particulate, the method may include measuring the molar charge of polymerization network modifiers in an amount of polymerizable material, whereby the molar charge of polymerization network modifiers is indicative of the reactivity of the polymerizable material in forming a geopolymer.

20 Claims, 4 Drawing Sheets

(51) Int. Cl.

| | |
|---|---|
| *G01N 23/207* | (2018.01) |
| *G01N 33/44* | (2006.01) |
| *C04B 40/00* | (2006.01) |
| *C04B 12/00* | (2006.01) |
| *C04B 7/00* | (2006.01) |
| *C04B 28/00* | (2006.01) |
| *C04B 32/00* | (2006.01) |
| *C04B 14/00* | (2006.01) |

(52) U.S. Cl.
CPC ......... *G01N 23/207* (2013.01); *G01N 33/442* (2013.01); *Y02P 40/165* (2015.11)

(56) References Cited

U.S. PATENT DOCUMENTS

| | | | |
|---|---|---|---|
| 5,853,475 | A | 12/1998 | Liskowitz et al. |
| 8,172,940 | B2 | 5/2012 | Boxley et al. |
| 8,177,906 | B2 | 5/2012 | Boxley |
| 2011/0052921 | A1* | 3/2011 | Gong ................ C04B 18/08 428/426 |
| 2012/0012034 | A1 | 1/2012 | Guynn |
| 2012/0085263 | A1 | 4/2012 | Guynn |

OTHER PUBLICATIONS

International Search Report (issued on PCT application from which the U.S. Application is derived). Report dated May 9, 2014.
Ahmaruzzaman, M., 2010. "A review on the utilization of fly ash." Progress in Energy and Combustion Science, 36 (3), pp. 327-363.
Bakharev, T., 2005. "Geopolymeric materials prepared using Class F fly ash and evaluated temperature curing." Cement and Concrete Research, 35, pp. 1224-1232.
Bonvin, D., Yellepeddi, R. & Buman, A., 2000. Application and perspectives of a new innovative XRF-XRD spectrometer in industrial process control. JCPDS—International Centre for Diffraction Data 2000, Advances in X-ray Analysis, 42, pp. 126-136.
Brantley, S.L., 2008. "Kinetics of Mineral Dissolution". Chapter 5 of Kinetics of Water-Rock Interaction, edited by Brantley, S. L., Kubicki, J.D. and White, A.F. Springer USA.
Bumrongjaroen, W., Muller, I., et al., 2007. "Application of glass corrosion tests to the reactivity of fly ash." In World of Coal Ash (WOCA), Northern Kentucky, USA.
Bumrongjaroen, W., Muller, I.S., et al., 2007. Characterization of Glassy Phase in Fly Ash From Iowa State University. (Technical Report) Used in Development of Performance Properties of Ternary Mixes: Transportation Pooled Fund Program of USDOT/FHWA, VSL-07R520.
Chen, C., et al. 2011. "Kinetics of fly ash leaching in strongly alkaline solutions." J Mater Sci, 46, pp. 590-597.
Cormier, L., Calas, G. & Cuello, G., 2010. Structural study of Ca—Mg and K—Mg mixing in silicate glasses by neutron diffraction. Journal of Non-Crystalline Solids, 356, pp. 2327-2331.
Criado, M., Palomo, A. & Fernandez-Jimenez, A., 2005. "Alkali activation of fly ashes. Part 1: Effect of curing conditions on the carbonation of the reaction products." Fuel, 84(16), pp. 2048-2054.
Crouch, L., Hewitt, R. & Byard, B., 2007. "High Volume Fly Ash Concrete." In World of Coal Ash (WOCA) Northern Kentucky, USA.
Diaz, E. I. et al., 2010. "Factors affecting the suitability of fly ash as source material for geopolymers." Fuel, 89, pp. 992-996.
Diaz-Loya, E.I., Allouche, E.N. & Vaidya, S., 2011. "Mechanical Properties of Fly-Ash-Based Geopolymer Concrete." ACI Materials Journal, 108(3), pp. 300-306.
Dombrowski, K. & Buchwald, A., 2007. "The influence of calcium content on the structure and thermal performance of fly ash based geopolymers." Journal of materials science, 42, pp. 3033-3043.
Duxson, P., et al. 2007. "Geopolymer technology: the current state of the art." Journal of materials science, 42, pp. 2917-2933.

Ehrman, S., Friedlander, S. & Zachariash, M., 1999. "Phase segregation in binary SiO2/TiO2 and SiO2/Fe2O3 nanoparticle aerosols formed in a premixed flame." Journal of materials research, 14(12), pp. 4551-4561.
Fernandez-Jimenez, A. et al., 2006. "Quantitative determination of phases in the alkai activation of fly ash. Part I. Potential ash reactivity." Fuel, 85, pp. 625-634.
Guillot, B. & Sator, N., 2007. "A computer simulation study of natural silicate melts. Part I: Low pressure properties." Geochimica et cosmochimica acta, 71, pp. 1249-1265.
Hwang, J.Y., Sun, X. & Li, Z., 2002. "Unburned Carbon from Fly Ash for Mercury Adsorption: I. Separation and Characterization of Unburned Carbon." Journal of Minerals & Materials Characterization & Engineering, I (I), pp. 39-60.
Katz, A., 1998. "Microscopic Study of Alkali-Activated Fly Ash." Cement and Concrete Research, 28, pp. 197-208.
Keller, W.D. 1954. "The bonding energies of some silicate minerals." Am Mineralogist, 39 pp. 783-793.
Keyte, L., 2008. "What's wrong with Tarong? The importance of coal fly ash glass chemistry in inorganic polymer synthesis", Doctor of Philosophy thesis, The University of Melbourne, Australia. 2008. The University of Melbourne.
Kumar, S. & Kumar, R., 2011. "Mechanical activation of fly ash: Effect on reaction, structure and properties of resulting geopolymer." Ceramics International, 37(2), pp. 533-541.
Lloyd, R.R., Provis, J.L. & Van Deventer, J.S.J., 2009. "Microscopy and microanalysis of inorganic polymer cements. 1: remnant fly ash particles." Journal of materials science, 44, pp. 608-619.
Mogus-Milankovic, A. et al. 2003. "Spectroscopic investigation of MoO3—Fe2O3—P2O5 and SrO—Fe2O3—P2O5 glasses." Part 1. Journal of Non-Crystalline Solids, 325, pp. 76-84.
Mysen, B.O. & Virgo, D., 1985. "Iron-bearing silicate melts: Relations between pressure and redox equilibria." Physics and Chemistry of Minerals, 12(4), pp. 191-200.
Pietersen, H.S. et al. 1989. "Reactivity of Fly Ash at High pH." Mat. Res. Soc. Symp. Proc., 178, pp. 139-157.
Provis, J. et al., 2009. "Valorasation of fly ashes by geopolymerisation." Global NEST Journal, 11(2), pp. 147-154.
Rao, J.B., Narayanaswami, P. & Prasad K.S., 2010. "Thermal stability of nano structured fly ash synthesized by high energy ball milling." International Journal of Engineering, Science and Technology, 2(5), pp. 284-299.
Ramachandran, S. et al. 1997. "Atomistic Simulations of Oleic Imidazolines Bound to Ferric Clusters." J. Phys. Chem. A, 101, pp. 83-89.
Rickard, W.D. a. et al., 2011. "Assessing the suitability of three Australian fly ashes as an aluminosilicate source for geopolymers in high temperature applications." Materials Science and Engineering: A, 528(9), pp. 3390-3397.
Temuujin, J., Williams, R. & Van Riessen, A., 2009. "Effect of mechanical activation of fly ash on the properties of geopolymer cured at ambient temperature." Journal of Materials Processing Technology, 209(12-13), pp. 5276-5280.
Weigel, C. et al., 2008. "Intermediate-range order in the silicate network glasses NaFexAl1-xSi2O6 (x=0,0.5,0.8,1): A neutron diffraction and empirical potential structure refinement modeling investigation." Phys. Rev. B, 78, pp. 064202-064212.
Weigel, C. et al. 2008. "Nature and distribution of iron sites in a sodium silicate glass investigated by neutron diffraction and EPSR simulation." Journal of Non-Crystalline Solids, 354, pp. 5378-5385.
Westrich, H.R. et al., 1993. "The dissolution kinetics of mixed-cation orthosilicate minerals." American Journal of Science, 293, pp. 869-893.
Williams, R. & Van Riessen, A., 2010. "Determination of the reactive component of fly ashes for geopolymer production using XRF and XRD." Fuel, 89, pp. 3683-3692.
Velbel, M.A., 1999. "Bond strength and the relative weathering rates of simple orthosilicates. American Journal of Science", 299, pp. 679-696.

* cited by examiner

ASSESSMENT METHOD

TECHNICAL FIELD

The present invention relates, inter alia, to a method of assessing the reactivity of a polymerizable material (especially an aluminosilicate) in forming a geopolymer. The present invention also relates to methods of forming a geopolymer, and to geopolymers formed by the method.

BACKGROUND ART

It will be clearly understood that, if a prior art publication is referred to herein, this reference does not constitute an admission that the publication forms part of the common general knowledge in the art in Australia or in any other country.

Geopolymers are synthetic materials produced by polymerization of a polymerizable material under alkaline conditions. These materials can provide comparable performance to traditional cements or concretes, and can also exhibit properties including high compressive strength, low shrinkage, fast or slow setting, acid resistance, fire resistance and low thermal conductivity.

Geopolymers also have an added advantage in that they can be produced from waste materials such as fly ash. Fly ash is an aluminosilicate fine particle residue collected from flue gas after the combustion of coal in a coal-fired power station. Globally more than 500 million tonnes of fly ash is produced annually, and a substantial amount is disposed of in landfills and/or lagoons. Fly ashes may be classified under ASTM C-618 into Classes F, C and N.

However, when for example fly ashes are used to make geopolymers, there can be a wide variation in the mechanical properties of the geopolymers formed. For example, Diaz-Loya et al (2011) studied the mechanical properties of geopolymer concretes made from different fly ashes collected from power stations across the United States. The result showed that the geopolymers made from 11 Class F fly ashes had an average compressive strength of approximately 36 MPa, while the geopolymers made from the remaining 11 Class C fly ashes had an average compressive strength of approximately 50 MPa. One geopolymer from a Class C fly ash only achieved a compressive strength of 2.73 MPa while some geopolymers from Class F fly ashes exhibited compressive strengths around 12 MPa. Three fly ashes were excluded as they were neither Class F or Class C according to their $SO_3$ content and particle size distribution.

Other researchers have also found similar variations when Australian fly ashes from different sources were used to make geopolymers. When the same activation and curing conditions were used, some fly ashes generated geopolymers with high compressive strength while other fly ashes were poorly activated and were unsuccessful in forming geopolymers (Keyte 2008; Provis et al. 2009).

A reason for the large variation in the geopolymer products is the highly heterogeneous nature of fly ash. It is reported that there are more than 13 identifiable phases in a fly ash, including $C_3A$-rich glass and low-silica glass (which are the main phases in high-calcium fly ash) and mullite-rich glass and Class F glass (which are the main phases in low-calcium fly ash) (Bumrongjaroen, et al. 2007). Furthermore, the mineral in coal powder varies from one power plant to another, even from time to time at the same plant, and the temperature inside the boiler may vary from 800 to 1400° C. Consequently, the collected fly ash may vary significantly in particle size, shape and composition.

Therefore, it is difficult to predict what properties a geopolymer will have, based on the starting materials used in the geopolymerization reaction.

One method to quantify the reactivity of fly ashes for geopolymer synthesis is described in US2011052921, which provides a procedure to quantify the reactivity of fly ashes in alkaline solutions as a function of pH and temperature. In this document, the fly ashes were characterized by their reactivity, measured in terms of the reaction progress which is the relative mass of reacted glass in alkali hydroxide solution as a function of time. However, this procedure requires reactions to be performed on the fly ash samples over periods of up to 14 days, and at temperatures of up to 75° C., before filtering, drying, washing, filtering and then drying the sample. This procedure can be time-consuming, and the measured reactivity may be affected by many variables including the molarity and kind of alkali in the alkali hydroxide solution, the temperature and the water-to-solid-ratio.

Other methods have focused on manipulating the activation conditions to achieve the desired geopolymer properties, such as the maximum mechanical properties. This may include manipulating the activator, additives and/or the curing temperature (Bakharev 2005; Criado, Palomo, and Fernández-Jimenez 2005; Dombrowski and Buchwald 2007). However, these conditions may require manipulation for each fly ash used.

Consequently, in one aspect an object of the present invention is to provide a method of assessing the reactivity of a polymerizable material in forming a geopolymer, based on the properties of the polymerizable material alone. In further aspects, an object of the present invention is to overcome one or more of the difficulties discussed above or to provide the consumer with a useful or commercial choice.

SUMMARY OF INVENTION

With the foregoing in view, the present invention in one form, resides broadly in a method of assessing the reactivity of a polymerizable material in forming a geopolymer. The polymerizable material may especially be fly ash.

In a first aspect, the present invention relates to a method of assessing the reactivity of a polymerizable material in forming a geopolymer, the method including the steps of:

Assessing whether the polymerizable material is layered or particulate; and

If the polymerizable material is layered, determining (especially measuring) the moles of polymerization network forming elements in an amount of polymerizable material, whereby the moles of polymerization network forming elements is indicative of the reactivity of the polymerizable material in forming a geopolymer; or If the polymerizable material is particulate, determining (especially measuring) the molar charge of polymerization network modifiers in an amount of polymerizable material, whereby the molar charge of polymerization network modifiers is indicative of the reactivity of the polymerizable material in forming a geopolymer.

In one embodiment, the reactivity of the polymerizable material in forming a geopolymer increases as the moles of polymerization network forming elements increases, or as the molar charge of polymerization network modifiers increases.

Advantageously, this method allows the reactivity of a polymerizable material in forming a geopolymer to be assessed based on only the chemical composition of a polymerizable material.

As used herein, the term "measuring" (as in, for example, measuring the moles of polymerization network forming elements or measuring the molar charge of polymerization network modifiers) means that the value is measured by experimental (especially chemical) techniques, especially quantitative chemical techniques. Examples of such techniques are discussed herein below.

As used herein, the phrase "reactivity of a polymerizable material in forming a geopolymer" refers to the extent to which the polymerizable material is able to participate in the geopolymerization reaction. The geopolymerization reaction is performed under the polymerization conditions (as herein, the "Polymerization Conditions"). In the Polymerization Conditions the polymerizable material is polymerized under alkaline activation conditions at temperatures less than 200° C. The temperature of the Polymerization Conditions may be less than 150° C. or less than 120° C., more especially less than 100° C. or 80° C., most especially less than 60° C. or 40° C. or 30° C. The temperature of the Polymerization Conditions may also be ambient temperature. The polymerizable material may be polymerized by treatment with an alkali metal or alkaline earth hydroxide or silicate. The alkali metal hydroxide may be selected from one or more of lithium hydroxide, sodium hydroxide and potassium hydroxide; especially one or more of sodium hydroxide and potassium hydroxide. The alkaline earth hydroxide may be selected from one or more of beryllium hydroxide, magnesium hydroxide and calcium hydroxide; especially one or more of magnesium hydroxide and calcium hydroxide. The alkali metal silicate may be selected from one or more of lithium silicate, sodium silicate and potassium silicate; especially one or more of sodium silicate and potassium silicate. The alkaline earth silicate may be selected from one or more of beryllium silicate, magnesium silicate and calcium silicate; especially one or more of magnesium silicate and calcium silicate. Combinations of an alkali metal or alkaline earth hydroxide or silicate may also be used. The alkali metal or alkaline earth hydroxide or silicate may be used as a solid or in a solution (especially an aqueous solution) in the Polymerization Conditions. Alkali metal or alkaline earth hydroxide or silicate may each be used, for example, in a range of 1 to 15 mol/L during the geopolymerization reaction, especially 2 to 12 mol/L, more especially 2 to 8 mol/L, most especially 2 to 5 mol/L. The alkali metal or alkaline earth hydroxide or silicate may be used in a range of 1-20% in terms of the mass ratio of $M_2O$ (M=Li, Na, K) and/or MO (M=Ca, Mg) to total solid materials. Further agents may also be included in the Polymerization Conditions, including silica fume, sodium aluminates, potassium aluminates and calcium aluminates. Sodium, potassium and calcium aluminates may be used to alter the ratio of Al to Si in the geopolymerization of the polymerizable material. Silica fume may also be used to alter the ratio of Al to Si in the geopolymerization of the polymerizable material, but it also may be used as a foaming agent to introduce air into the geopolymer and reduce its density. Alumina powder may be used as foaming agent to form fine bubbles for the manufacturing of foam geopolymer concretes under ambient to 200° C. conditions and this may also used to alter the ratio of Al to Si.

The term "geopolymer" refers to a material produced by polymerization of a polymerizable material containing silicon or aluminium (or a blend of two or more polymerizable materials), under alkaline activation conditions. As discussed above, the polymerization is performed under the Polymerization Conditions. The geopolymer may be one or more of a geopolymer paste, a geopolymer mortar and a geopolymer concrete. The geopolymer can be a dense concrete or a foam concrete. The geopolymer may especially be a geopolymer concrete. Other names for geopolymer may include: low-temperature aluminosilicate glass, alkali-activated cement, geocement, alkali-bonded ceramic, inorganic polymer concrete and hydroceramic.

The term "polymerizable material" refers to any material including aluminium or silicon that is capable of polymerizing to form a geopolymer. In one embodiment, the polymerizable material includes both aluminium and silicon; and the polymerizable material especially may be an aluminosilicate, including both aluminium and silicate. In one embodiment, the polymerizable material is a solid. In one embodiment, the polymerizable material includes one or more of polymerization network forming elements, polymerization network modifiers and polymerization network modifying iron.

In one embodiment, the polymerizable material is a pozzolan A "pozzolan" is a siliceous and aluminous material, which is able to react under alkaline conditions to form compounds possessing cementitious properties. The pozzolan especially reacts to form the compounds at temperatures below 100° C., especially below 50° C., more especially at 15-35° C., most especially at about 25° C. The pozzolan reacts under alkaline conditions.

In another embodiment, the polymerizable material is selected from layered and particulate polymerizable materials. Layered polymerizable materials may be selected from heated clays, including a 2:1 layer lattice aluminosilicate (such as metakaolin), and a 1:1 layer lattice aluminosilicate; especially a 2:1 layer lattice aluminosilicate; more especially metakaolin. Particulate polymerizable materials may be selected from silica fume, superfine silica powder, slag (especially granulated slag), fly ash, combustion ash (such as fluidized bed combustion bottom ash and coal combustion bottom ash), treated reservoir sludge, waste and prepared aluminosilicate, and non-iron and iron-bearing glasses; especially slag and fly ash; most especially fly ash. A fly ash may be selected from a high calcium containing fly ash, Class C fly ash, Class F fly ash and Class N fly ash; especially Class C and Class F fly ash. Silica fume and superfine silica powder are examples of polymerizable materials that include Si, and these materials may also include small amounts of Al. Metakaolin, fly ash, fluidized bed combustion bottom ash, treated reservoir sludge, slag, coal combustion bottom ash waste and prepared aluminosilicate are all examples of polymerizable materials that typically include both Al and Si.

The reactivity of the polymerizable material typically affects the properties of the geopolymer formed from the polymerizable material. In one embodiment, the reactivity of the polymerizable material correlates with, and especially is proportional to, one or more mechanical properties of the geopolymer formed from the polymerizable material. For example, as the reactivity of the polymerizable material increases, then so may one or more mechanical properties of a geopolymer formed from the polymerizable material. The mechanical properties of the geopolymer may be selected from one or more of the compressive strength, flexural strength, bending strength, tension strength and compression modulus of the geopolymer. For example, a polymerizable material with a higher reactivity may form a geopolymer with increased strength, especially increased compressive strength, increased flexural strength and/or increased compression modulus. In one embodiment, as the reactivity of the polymerizable material increases, then the geopolymer formed from the polymerizable material is predicted to possess one or more of: increased compressive strength, increased flexural strength, increased bending strength, increased tension strength and increased compression modulus.

Compressive strength can be measured using a hydraulic compression machine, and standards such as ASTM C109/109M may be used for a cubic sample, and ASTM C579-01 may be used for small cylinder samples. The compression modulus can also be calculated from the stress-strain curves. Flexural strength may be assessed for mortar specimens using ASTM C 348-08, and for mortars, grouts, monolithic surfacings and polymer concretes using ASTM C580-02.

The method of the first aspect of the present invention includes the step of assessing whether a polymerizable material is particulate or layered. A skilled person may be able to perform this step without any specialised equipment, as that person may know that metakaolin, for example, is a layered polymerizable material, whereas a fly ash is a particulate polymerizable material. Other examples of layered and particulate polymerizable materials are provided above. Alternatively, a skilled person may use equipment such as a scanning or transmission electron microscope to assess the structure of the polymerizable material.

If the polymerizable material is layered, then the reactivity of the polymerizable material in forming a geopolymer may be assessed by determining the moles of polymerization network forming elements in an amount of polymerizable material. In this case, the moles of polymerization network forming elements is indicative of the reactivity of the layered polymerizable material in forming a geopolymer. In one embodiment, as the moles of polymerization network forming elements increases, then so does the reactivity of the polymerizable material.

As used herein, the term "polymerization network forming elements" refers to elements within compounds (such as Al in $Al_2O_3$) that are capable of acting as network formers when reacted under the Polymerization Conditions, preferably at temperatures below 60° C. As used herein, the term "polymerization network forming elements" does not include iron. In one embodiment, the polymerization network forming elements include one or more of silicon (Si), aluminium (Al) and phosphorous (P); especially Si and Al (especially $Al^{IV}$). Typically the polymerization network forming elements are in the amorphous phase of the polymerizable material. This is because crystalline phases in the polymerizable material are typically not or much less reactive than amorphous phases under the Polymerization Conditions. For example, the moles of polymerization network forming elements from $Al_2O_3$ in an amount of polymerizable material would be 2 times the number of moles of $Al_2O_3$ in the amount of polymerizable material.

Alternatively, if the polymerizable material is particulate, then the reactivity of the polymerizable material in forming a geopolymer may be assessed by determining the molar charge of polymerization network modifiers in an amount of polymerizable material. In this case, the molar charge of polymerization network modifiers is indicative of the reactivity of the polymerizable material in forming a geopolymer. In one embodiment, as the molar charge of polymerization network modifiers increases, then so does the reactivity of the polymerizable material.

The tee n "polymerization network modifiers" refers to compounds that are capable of acting as network modifiers under the Polymerization Conditions, preferably at temperatures below 60° C. Network modifiers do not form networks, but alter the network structure of the geopolymer under the Polymerization Conditions. Network modifiers decrease the polymer degree of the geopolymer structure. As used herein, the term "polymerization network modifiers" does not include iron compounds. In one embodiment, the polymerization network modifiers include compounds of alkali metal and alkaline earth elements, such as one or more of CaO, MgO, $K_2O$ and $Na_2O$; especially two or more of CaO, MgO, $K_2O$ and $Na_2O$; more especially three or more of CaO, MgO, $K_2O$ and $Na_2O$; most especially all of CaO, MgO, $K_2O$ and $Na_2O$. Typically, the polymerization network modifiers are in the amorphous phase of the polymerizable material. This is because crystalline phases in the polymerizable material are typically not or much less reactive under the Polymerization Conditions.

For example, the molar charge of polymerization network modifiers from CaO, MgO, $K_2O$ and $Na_2O$ in an amount of polymerizable material would be 2 times the number of moles of CaO and MgO (as Ca is $Ca^{2+}$ and Mg is $Mg^{2+}$), and 2 times the number of moles of $K_2O$ and $Na_2O$ (as K is $K^+$ and Na is $Na^+$) in the amount of polymerizable material.

For particulate polymerizable materials, the reactivity of the polymerizable material may also be affected by the presence of polymerization network modifying iron in the material. Therefore, in one embodiment, the method further includes the step of determining the molar charge of polymerization network modifying iron in the amount of particulate polymerizable material, whereby the molar charge of polymerization network modifying iron is indicative of the reactivity of the polymerizable material in forming a geopolymer. In one embodiment, as the molar charge of polymerization network modifying iron increases, then the reactivity of the polymerizable material in forming a geopolymer also increases. In another embodiment, the sum of the molar charge of polymerization network modifying iron and the molar charge of polymerization network modifiers in the amount of particulate polymerizable material is indicative of the reactivity of the polymerizable material in forming a geopolymer. In one embodiment, the reactivity of the polymerizable material in forming a geopolymer increases as there is an increase in the sum of the molar charge of polymerization network modifying iron and the molar charge of polymerization network modifiers.

As used herein, the term "polymerization network modifying iron" refers to iron in the polymerizable material which is capable of acting as a network modifier under the Polymerization Conditions, preferably at temperatures below 60° C.

The molar charge of polymerization network modifying iron from $Fe_2O_3$ in a polymerizable material can be determined by multiplying the number of moles of $Fe_2O_3$ in the material by 6 ($2 \times Fe^{3+}$). However, and without wishing to be bound by theory, it is believed that only the portion of $Fe^{3+}$ and $Fe^{2+}$ in the polymerizable material that is 5-coordinated will tend to act as network modifiers. Therefore, in one embodiment the molar charge of polymerization network modifying iron in the amount of polymerizable material is the molar charge of 5-coordinated $Fe^{3+}$ and $Fe^{2+}$.

The portion of $Fe^{3+}$ and $Fe^{2+}$ in the polymerizable material that is 5-coordinated can be determined using high-resolution neutron diffraction combined with structural modelling using the Empirical Potential Structure Refinement (EPSR) code (Weigel et al. 2008). Alternatively, the portion of $Fe^{3+}$ and $Fe^{2+}$ in the polymerizable material that is 5-coordinated can be approximated by considering the results of Weigel et al. 2008. Fitting a straight line to the results provided in Weigel provides the following equations which may be used to approximate the portion of 5-coordinated $Fe^{3+}$ and $Fe^{2+}$ in the polymerizable material:

$$\text{mol Fe}^{3+} = \text{mol Fe}\left(\left(89.42 - 1.732\left(\frac{\text{molar charge of polymerization network modifiers}}{\text{mol Fe}}\right)\right)\bigg/100\right) \quad (1)$$

$$\text{mol Fe}^{2+} = \text{mol Fe} - \text{mol Fe}^{3+} \quad (2)$$

$$^{[5]}\text{Fe ratio} = \left(91.75 - 59.23\left(\frac{\text{molar charge of polymerization network modifiers}}{(\text{mol Fe} + \text{mol Al})}\right)\right)\bigg/100 \quad (3)$$

$$\text{molar charge }^{[5]}\text{Fe}^{2+} + \text{molar charge }^{[5]}\text{Fe}^{3+} = \quad (4)$$
$$^{[5]}\text{Fe ratio }(3(\text{mol Fe}^{3+}) + 2(\text{mol Fe}^{2+}))$$

In these equations, mol $Fe^{3+}$, mol $Fe^{2+}$, mol Fe, mol Al, molar charge of polymerization network modifiers, molar charge of $^{[5]}Fe^{2+}$ and molar charge of $^{[5]}Fe^{3+}$ are all calculated for an amount of polymerizable material. Mol Fe is the total number of moles of polymerizable iron in the amount of polymerizable material, and mol Al is the total number of moles of polymerizable aluminium in the amount of polymerizable material. The term "polymerizable iron" refers to the amount of iron that is capable of participating in the polymerization reaction, and the "polymerizable aluminium" refers to the amount of aluminium that is capable of participating in the polymerization reaction. In one embodiment, the polymerizable iron and the polymerizable aluminium is the iron or aluminium in the amorphous phase of the polymerizable material.

As used herein, the phrase "amount of polymerizable material" refers to a sample containing a defined (possibly arbitrary) amount of polymerizable material. For example, if the chemical composition of the polymerizable material is determined in wt %, it may be advantageous to determine the moles of polymerization network forming elements or the molar charge of polymerization network modifiers per 100 g of polymerizable material. When comparing the reactivity of different polymerizable materials the same amount of each polymerizable material should be used (this may be achieved by calculating a molar percentage of the polymerization network forming elements, for example).

Without wishing to be bound by theory, it is believed that the networking formers in a polymerizable material (for layered polymerizable materials), and the network modifiers in a polymerizable material (for particulate polymerizable materials) allows the reactivity of a polymerizable material to be assessed due to the bond energies between oxygen and the network formers or modifiers in the polymerizable material.

For example, typical bond energies for particulate polymerizable materials may be as follows: Si—O 4,000 kJ/mol, Al—O 2,500 kJ/mol, Na—O 300 kJ/mol, K—O 500 kJ/mol, and Ca—O 800 kJ/mol. This means that for particulate polymerizable materials the bonds between oxygen and the network modifiers (Na, K, Ca) are all weaker than the bonds between oxygen and the network formers (Al and Si). Therefore, the network formers will react preferentially in a geopolymerization reaction.

In contrast, for layered polymerizable materials the bond energies for Si—O and Al—O bonds are reduced because these polymerizable materials have typically been heated. This makes the Si—O and Al—O bonds more likely to react in a geopolymerization reaction.

In a further embodiment, the method includes the step of providing (especially determining, and more especially measuring) the surface area of the polymerizable material, whereby the reactivity of the polymerizable material in forming a geopolymer increases as the surface area increases. In one embodiment, the surface area of the polymerizable material may be multiplied by: (i) (for layered polymerizable materials) the moles of polymerization network forming elements in the amount of polymerizable material; or (ii) (for particulate polymerizable materials) the molar charge of polymerization network modifiers in the amount of polymerizable material, or the sum of the molar charge of polymerization network modifiers and the molar charge of polymerization network modifying iron in the amount of polymerizable material. The result of this calculation is indicative of the reactivity of the polymerizable material in forming a geopolymer. In one embodiment, as the result of this calculation increases, then the reactivity of the polymerizable material also increases. An exemplary surface area for a metakaolin may be, for example, 10 $m^2/g$, and an exemplary surface area for a fly ash may be, for example, 0.5 to 2.5 $m^2/g$.

The surface area of the polymerizable material may be determined using a particle size analyzer or by Gas absorption via the Brunauer-Emmett-Teller (BET) method. When using a particle size analyser, the surface area (SA) can be calculated from the results of the particle size distribution measurement using the following equation:

$$SA = (6\Sigma(V_i/d_i))/(\rho\Sigma V_i) = 6/(\rho D[3,2])$$

in which: $V_i$ is the relative volume in class i with a mean class diameter of $d_i$, $\rho$ is the density of the material, and $D[3,2]$ is the surface area weighted mean diameter. Alternatively, if the BET absorption method is used, the surface area can be calculated from the results of a molecular absorption regression curve.

In another embodiment, the method includes the step of milling the polymerizable material. Milling can break down large particles and increase the surface area of the particles. Therefore, milling can increase the reaction rate and extent of reaction of the polymerizable material. For example, for some fly ashes a long milling process may change the phase or crystallinity. However, milling for a suitable period using a ball mill or a vibration mill should not change the phase state of the fly ash too much. For example, by milling fly ash for 60 min, the compressive strength of geopolymers formed may increase by greater than 80%, mainly due to increased surface area.

In a further embodiment, the method further includes the step of providing the chemical composition of the polymerizable material, especially the chemical composition of the amorphous phase of the polymerizable material. In another embodiment, the method further includes the step of measuring the chemical composition of the polymerizable material, especially the chemical composition of the amorphous phase of the polymerizable material. The chemical composition of the polymerizable material may be measured by X-Ray Fluorescence (XRF) and/or quantitative X-Ray Diffractometry (Q-XRD). When both of these methods are used, the chemical composition of the amorphous phase of the polymerizable material may be determined, which may allow calculation of: (i) (for layered polymerizable materials) the moles of polymerization network forming elements in an amount of polymerizable material; or (ii) (for particulate polymerizable materials) the molar charge of polymerization network modifiers in an amount of polymerizable material, and optionally the molar charge of polymerization network modifying iron in the amount of polymerizable material. As discussed above, crystalline phases in the polymerizable material are typically not or much less reactive than amorphous phases under the Polymerization Conditions. In a further embodiment, the method further includes the step of measuring the moles of polymerization network forming elements in an amount of polymerizable material. In another embodiment, the method further includes the step of measuring the molar charge of polymerization network modifiers in an amount of polymerizable material.

Q-XRD allows the phases present in the polymerizable material to be analysed. Alternatively, the amount of amorphous phase in the polymerizable material can be determined using an alkaline solution to completely dissolve the amorphous (glass) phase. XRF allows the chemical composition of the polymerizable material to be measured.

XRF may provide the results in two forms: the amount of each element in the material, or the amount of each element in the form of oxides in the material. The results of XRF when provided in either form may be used in the method of the present invention. However, references to oxides (such as $Al_2O_3$ and $Fe_2O_3$) throughout the summary of the invention typically refer to amounts derived from the results of XRF, as provided in the form of oxides. As discussed above, polymerizable materials such as fly ash can be very complex, and referring to the elements in the polymerizable material in oxide form conveniently simplifies discussion.

Therefore, in one embodiment of the present invention there is provided a method of calculating the reactivity of a polymerizable material in forming a geopolymer, the method including the steps of:
 Assessing whether the polymerizable material is layered or particulate;
 Providing (especially measuring) the chemical composition of the polymerizable material;
 Providing (especially measuring) the surface area of the polymerizable material; and
 If the polymerizable material is layered, determining the moles of polymerization network forming elements in an amount of polymerizable material, and calculating the reactivity of the polymerizable material in forming a geopolymer by multiplying the surface area of the polymerizable material by the moles of polymerization network forming elements in the amount of polymerizable material; or
 If the polymerizable material is particulate, determining the molar charge of polymerization network modifiers in an amount of polymerizable material, and calculating the reactivity of the polymerizable material in forming a geopolymer by multiplying the surface area of the polymerizable material by the molar charge of polymerization network modifiers in the amount of polymerizable material.

If the polymerizable material is a particulate, this embodiment may further include the steps of:
 determining the molar charge of polymerizable network modifying iron in the amount of polymerizable material; and
 calculating the reactivity of the polymerizable material in forming a geopolymer by multiplying the surface area of the polymerizable material by the sum of the molar charge of polymerization network modifiers and the molar charge of polymerization network modifying iron in the amount of polymerizable material.

Therefore, in a second aspect the present invention provides a method of calculating the reactivity of a polymerizable material in forming a geopolymer, the method including the steps of:
 Providing:
  (i) If the polymerizable material is layered, the moles of polymerization network forming elements in an amount of polymerizable material;
  (ii) If the polymerizable material is particulate, the molar charge of polymerization network modifiers, and the molar charge of polymerization network modifying iron in the amount of polymerizable material; and
  (iii) the surface area of the polymerizable material; and
 Calculating the reactivity of the polymerizable material in forming a geopolymer by multiplying (iii) by:
  the moles of polymerization network forming elements, if the polymerizable material is layered; or
  the sum of the molar charge of polymerization network modifiers and the molar charge of polymerization network modifying iron, if the polymerizable material is particulate.

As discussed above, a skilled person may be able to perform the step of assessing whether the polymerizable material is layered or particulate without any specialised equipment, as that person may know that metakaolin (for example) is a layered polymerizable material. Consequently, in a third aspect the present invention provides a method of assessing the reactivity of a layered polymerizable material in forming a geopolymer, the method including the step of:
 Determining the moles of polymerization network forming elements in an amount of layered polymerizable material,
 whereby the moles of polymerization network forming elements is indicative of the reactivity of the layered polymerizable material in forming a geopolymer.

In one embodiment, as the moles of polymerization network forming elements increases, then the reactivity of the particulate polymerizable material also increases.

Further, in a fourth aspect the present invention provides a method of calculating the reactivity of a layered polymerizable material in forming a geopolymer, the method including the steps of:
 Providing: the moles of polymerization network forming elements in an amount of layered polymerizable material and the surface area of the layered polymerizable material; and
 Calculating the reactivity of the layered polymerizable material in forming a geopolymer by multiplying the surface area of the layered polymerizable material by the moles of polymerization network forming elements in an amount of layered polymerizable material.

Alternatively, a skilled person may know that a polymerizable material is particulate (for example fly ash). Therefore, in a fifth aspect the present invention provides a method of assessing the reactivity of a particulate polymerizable material in forming a geopolymer, the method including the step of:
 Determining the molar charge of polymerization network modifiers in an amount of particulate polymerizable material,
 whereby the molar charge of polymerization network modifiers is indicative of the reactivity of the particulate polymerizable material in forming a geopolymer.

In one embodiment, as the molar charge of polymerization network modifiers increases, then the reactivity of the particulate polymerizable material also increases.

Further, in a sixth aspect the present invention provides a method of calculating the reactivity of a particulate polymerizable material in forming a geopolymer, the method including the steps of:

Providing: the molar charge of polymerization network modifiers in an amount of particulate polymerizable material; the molar charge of polymerization network modifying iron in the amount of particulate polymerizable material; and the surface area of the particulate polymerizable material; and Calculating the reactivity of the particulate polymerizable material in forming a geopolymer by multiplying the surface area of the particulate polymerizable material by the sum of the molar charge of polymerization network modifiers in an amount of particulate polymerizable material and the molar charge of polymerization network modifying iron in the amount of particulate polymerizable material.

However, if the chemical composition of the polymerizable material (especially the amorphous phase of the polymerizable material) is provided in the form of oxides (for example), then it may not be necessary to determine the molar charge of polymerization network modifiers or the molar charge of polymerization network modifying iron. This is because if the polymerization network modifier compounds are, for example, CaO, MgO, $K_2O$ and $Na_2O$, then the molar charge of polymerization network modifiers will be 2 times the number of moles of CaO and MgO (as Ca is $Ca^{2+}$ and Mg is $Mg^{2+}$), and 2 times the number of moles of $K_2O$ and $Na_2O$ (as K is $K^+$ and Na is $Na^+$) in the amount of polymerizable material. Hence, as the number of moles of all polymerization network modifier compounds is multiplied by 2 to obtain the molar charge of polymerization network modifiers in the polymerizable material, simply determining the moles of polymerization network modifier compounds in an amount of polymerizable material will be equally accurate in assessing the reactivity of the polymerizable material.

Therefore, in a seventh aspect the present invention provides a method of assessing the reactivity of a particulate polymerizable material in forming a geopolymer, the method including the step of:

Determining the moles of polymerization network modifier compounds in an amount of particulate polymerizable material,
whereby the moles of polymerization network modifier compounds is indicative of the reactivity of the particulate polymerizable material in forming a geopolymer.

In one embodiment, as the moles of polymerization network modifier compounds increases, then so does the reactivity of the polymerizable material.

Features of the second, third, fourth, fifth, sixth and seventh aspects of the present invention may be as described for the first aspect of the present invention.

In an eighth aspect, the present invention provides a method of forming a geopolymer, the method including the steps of:

Providing a polymerizable material;

Assessing the reactivity of the polymerizable material by the method of the first, third, fifth, or seventh aspect of the present invention; or calculating the reactivity of the polymerizable material by the method of the second, fourth or sixth aspect of the present invention; and Polymerizing the polymerizable material to form a geopolymer.

In one embodiment, the method may include the step of measuring the chemical composition of the polymerizable material. This step may be as discussed above for the first aspect of the present invention. The step of polymerizing the polymerizable material to form a geopolymer may be as defined above for the Polymerizing Conditions.

In a further embodiment, the method of the eighth aspect may include the step of milling the polymerizable material, as discussed above in relation to the first aspect of the present invention.

In another embodiment, this method of the present invention may further include the step of mixing one or more additives with the polymerizable material, before or during polymerization. The one or more additives may be selected from one or more of a foaming agent (such as silica fume), a lightening additive (such as expanded polystyrene (EPS) particles or other lightweight mineral particles) or lightening admixture, a superplasticizer, an aluminosilicate salt, a mineral to reduce efflorescence, or chemical to improve the volume stability or chemical stability of a geopolymer. In one embodiment, a combination of additives may be mixed with the polymerizable material.

If the additive is a foaming agent, the method may include the further step of mixing preformed foam with a polymerization paste or mixing a foaming agent (such as $H_2O_2$ and Al powder) and raising bubbles within a polymerization paste, wherein the paste is formed by activating the polymerizable material under alkaline conditions. The method may also include the further step of mixing a lightening additive with a polymerization paste, wherein the paste is formed by activating the polymerizable material under alkaline conditions. Inclusion of voids and lightening additives or admixtures allows for production of a cellular geopolymer (which is porous) and multi-phase (especially low density phase). In this way, the density of the geopolymer may be decreased so that a light weight product is formed.

In another embodiment, the method further includes the step of mixing one or more superplasticizers (especially two or more superplasticizers) to increase the workability of the mixed paste, mortar or concrete; or mixing one or more aluminosilicate salts (especially two or more aluminosilicate salts) and minerals to reduce efflorescence; or mixing one or more chemicals (especially two or more chemicals) to improve the volume stability and chemical stability of the geopolymer.

By mixing additives with the polymerizable material before or during polymerization, geopolymer properties such as strength, thermal or acoustic efficiency and density may be optimised. The workability, physical stability or chemical stability of the geopolymer may also be improved.

In a ninth aspect, the present invention relates to a geopolymer when formed by the method of the eighth aspect of the present invention.

In a tenth aspect, the present invention relates to a reactivity of a polymerizable material in forming a geopolymer, when calculated by the method of the second, fourth or sixth aspects of the present invention. This aspect encompasses the use of computer programs to calculate the reactivity of the polymerizable material, and the reactivity can be provided in any visual or electronic output.

In an eleventh aspect, the present invention relates to a system configured to calculate the reactivity of a polymerizable material in forming a geopolymer according to the method of the second, fourth or sixth aspects of the present invention.

In a twelfth aspect, the present invention relates to a system or apparatus configured to assess the reactivity of a polymerizable material in forming a geopolymer according to the method of the first, third, fifth or seventh aspects of the present invention.

Any suitable system, including a conventional personal computer, may be used in the eleventh or twelfth aspect of the present invention.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

Any of the features described herein can be combined in any combination with any one or more of the other features described herein within the scope of the invention.

BRIEF DESCRIPTION OF DRAWINGS

Preferred features, embodiments and variations of the invention may be discerned from the following Description of Embodiments which provides sufficient information for those skilled in the art to perform the invention. The Description of Embodiments is not to be regarded as limiting the scope of the preceding Summary of Invention in any way. The Description of Embodiments will make reference to a number of drawings as follows.

DESCRIPTION OF EMBODIMENTS

Figure 1A:
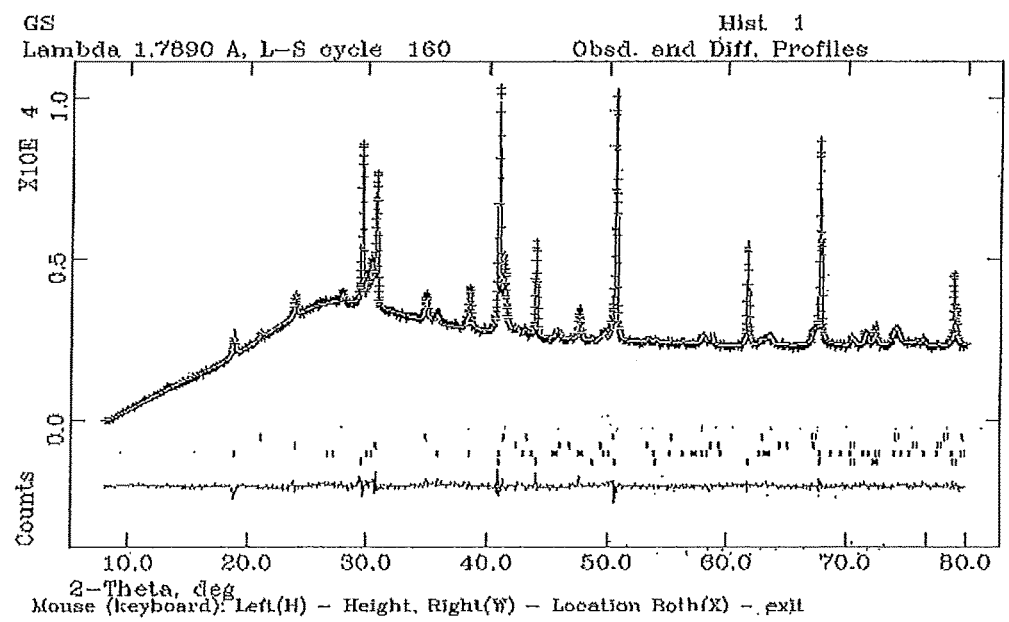
FIG. 1A refers to Fly Ash A, FIG. 1B to Fly Ash B, FIG. 1C to Fly Ash C, FIG. 1D to Fly Ash D, and FIG. 1E to Fly Ash E.
Figure 1B:
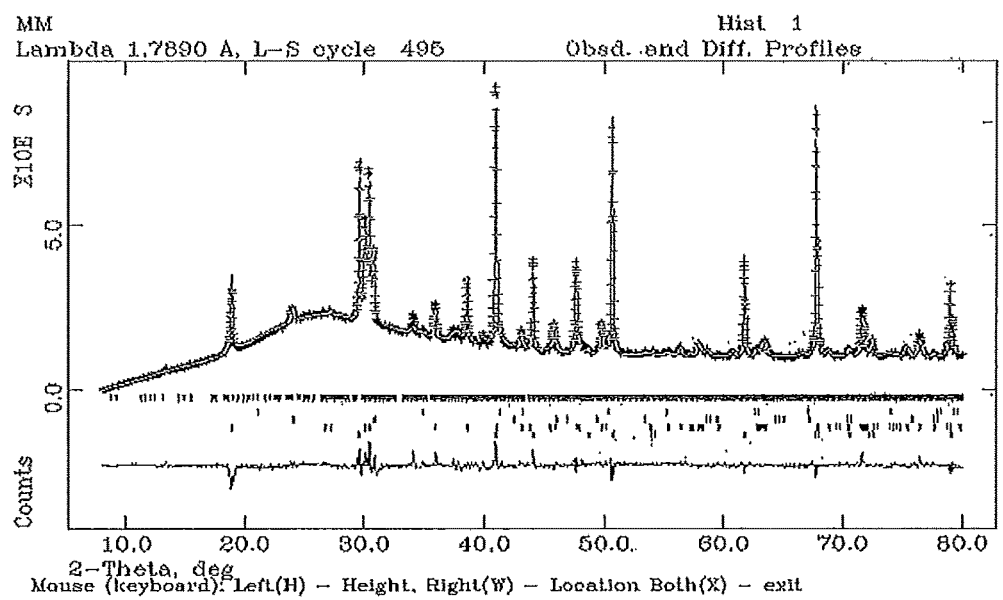
FIG. 1 shows the quantitative analysis of the five fly ash samples using Rietveld refinement XRD.
Figure 1C:
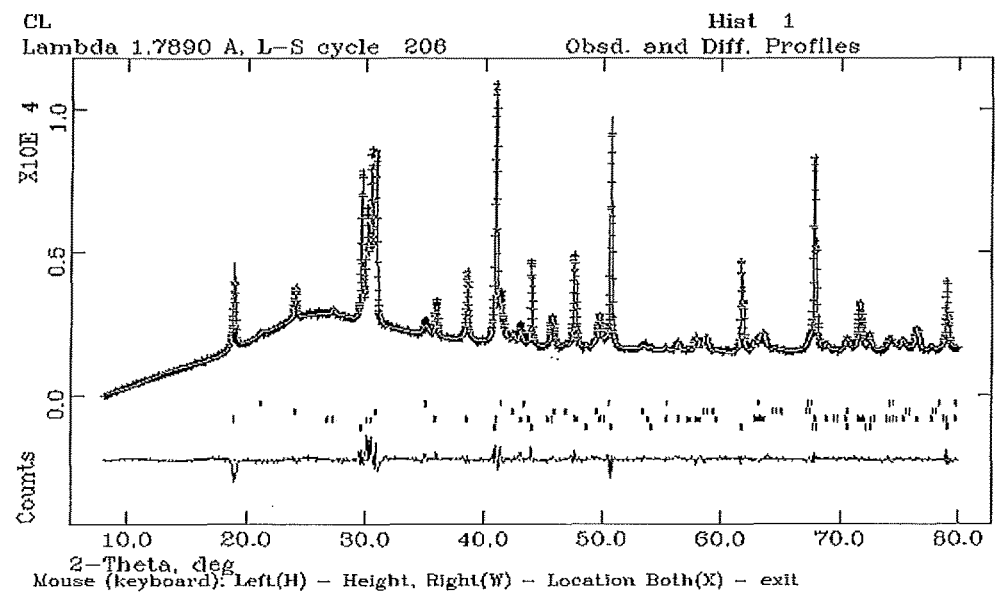
Figure 1D:
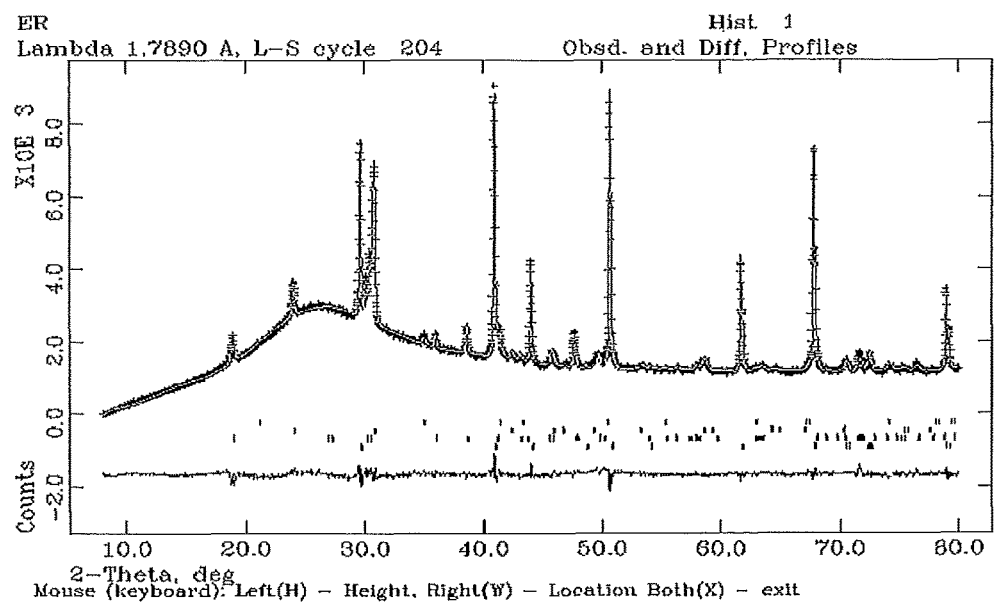
Figure 1E:
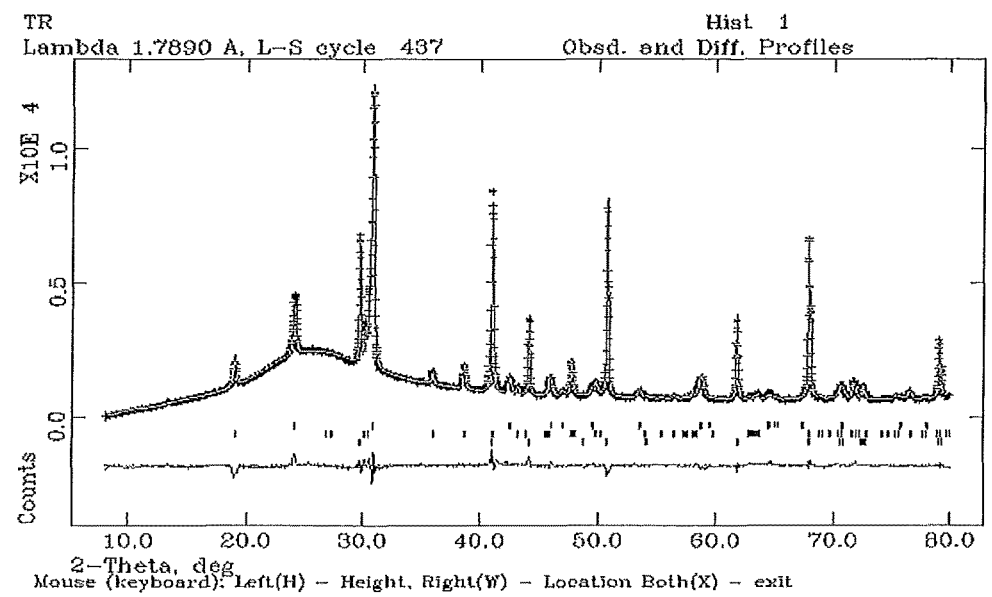

Chemistry of Polymerizable Materials, Especially of Fly Ash

Reactive Bonds

The amorphous phase of fly ash includes Si (a network former), and also Al and Fe which are of relatively high quantity. The impact of Al and Fe may be important when analysing the reactivity of fly ash from the view of its glass chemistry.

In $Fe_2O_3$—$SiO_2$ glasses, the state of iron seems to be more dependent on temperature rather than on chemical composition. Under 2000 K (1727° C.) Si and Fe tend to form crystobalite and liquid phase, while under 1730 K (1457° C.) Si and Fe tend to form separate phases, such as magnetite and tridymite or hematite and tridymite at lower temperature. This means that $Fe^{2+}$ and $Fe^{3+}$, regardless of their content, are 6-coordinated and have limited ability to substitute for Si in the glass network. During cooling, $Fe^{2+}$ and $Fe^{3+}$ favour phase segregation and becoming Fe enriched phases, and are not able to contribute significantly to the network structure.

However, the amorphous (glass) phase of fly ash contains a quantity of aluminium and alkali metal/alkaline earth ions. When aluminium, alkali metal and alkaline earth ions incorporate in silica glass, the state of iron will be changed in view of the charge balance capability of alkali metal and alkaline earth cations. In sodosilicate glasses with a composition of $NaFe_xAl_{1-x}Si_2O_6$, the majority of $Fe^{3+}$ is 4-coordinated and plays a network forming role, like most Al atoms. Both $FeO_4$ and $AlO_4$ are randomly distributed and connect with $SiO_4$ tetrahedra by sharing corners. Only a small fraction of $Fe^{3+}$ and $Fe^{2+}$ are 5-coordinated in the form of $FeO_5$, which tends to form clusters and to share edges with each other. When the amount of Fe in glass decreases, more Fe tends to be in a 4-coordinated state. For instance, in glass $NaFe_{0.5}Al_{0.5}Si_2O_6$, 66 mol % of Fe is 4-coordinated, 32 mol % of Fe is 5-coordinated and 2 mol % is in another state.

If it is assumed that:
1) the crystalline phases in fly ash are pure and non-active;
2) only the amorphous phase components undergo dissolution under the Polymerization Conditions;
3) the Al—O, Fe—O and Si—O bonds linked with network modifier are much weaker (i.e. more reactive) than Si—O—Si and Si—O—Al;
4) in the amorphous (glass) phase: both $Si^{4+}$ and $Ti^{4+}$ are 4-coordinated, playing the role of network former; $Ca^{2+}$, $Mg^{2+}$, $Na^+$ and $K^+$ preferably play the role of network modifier; and
5) in the amorphous (glass) phase Fe may be a network former or a network modifier (in particular some $Fe^{3+}$ cations act as network formers, and some are network modifiers), then the concentration of reactive bonds is:

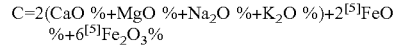

wherein CaO, MgO, $Na_2O$, $K_2O$, $^{[5]}FeO$ and $^{[5]}Fe_2O_3$ (5-coordinated FeO and 5-coordinated $Fe_2O_3$) is provided as molar percentages in the polymerizable material (or moles of each in 100 g of polymerizable material).

The total Fe content can be determined by XRF in the form of $Fe_2O_3$. The concentration of network modifier 5-coordinated Fe and its charge (both $Fe^{2+}$ and $Fe^{3+}$ present in aluminosilicate glasses) change according to the concentration of Fe and other elements in the glassy phase (Mysen & Virgo 1985), and its concentration may be quantified using neutron diffraction and Empirical Potential Structure Refinement (EPSR) modelling methods (Weigel et al. 2008). Alternatively, the portion of $Fe^{3+}$ and $Fe^{2+}$ in the polymerizable material that is 5-coordinated can be approximated by linearly fitting with the results of Weigel et al. 2008 (as discussed in the equations provided above).

The above assumptions may be applied to other particulate polymerizable materials. However, layered polymerizable materials have different chemical properties as the strength of Si—O and Al—O bonds are typically weaker. In these polymerizable materials the concentration of reactive bonds is:

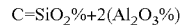

wherein $SiO_2$ and $Al_2O_3$ is provided as molar percentages in the polymerizable material (or moles of each in 100 g of polymerizable material).

Surface Area

The surface area (SA) may also affect the dissolution rate and final reaction extent of fly ash particles. Geopolymerization is not a simple solution reaction at high liquid/solid ratio; it is a complicated combination of solution reaction, solid dissolution reaction and solid reaction. It is not simple to provide an exact influence of the particle geometry. If considering compressive strength as an effective index indicating fly ash reactivity, the SA has a linear relationship with its reactivity.

Reactivity of Polymerizable Material (Especially Fly Ash)

The reactivity of a polymerizable material may be defined by multiplying the total molar percentage of reactive bonds in the glass phases by the surface area.

For particulate polymerizable materials, the reactivity may equal $[2 \,(CaO\% + MgO\% + Na_2O\% + K_2O\%) + 2^{[5]}Fe^{2+}\% + 6^{[5]}Fe^{3+}\%] \times SA$.

Alternatively, for layered polymerizable materials the reactivity may equal $[SiO_2\% + 2(Al_2O_3\%)] \times SA$.

The unit of this reactivity calculation is $m^2/g$, which is the unit of SA. This calculation provides an index for calculating the reactivity of a polymerizable material, especially a fly ash, for geopolymer synthesis. A polymerizable material with a higher reactivity should produce higher strength geopolymer products, if it is assumed that the activation and curing conditions for all tested polymerizable materials are identical.

Use of Polymerizable Materials in Forming Geopolymers Compared to Addition of Polymerizable Materials to Concrete Fly ash is used as a supplementary cementitious material in the production of Portland cement-based concretes, and fly ash is particularly used in high volume fly ash concretes, which usually contain more than 50% of fly ash by mass of total cementitious materials. However, fly ash is still only used in small quantities, around 16% of total ash. The reason for this is that cement and concrete makes poor use of the intrinsic reactivity of the glassy phases present in the fly ash. The cement and concrete industry is very selective in choosing fly ashes: only those with high reactivity (usually Class C) can be used in high volume.

In contrast, geopolymer production can use most fly ashes as the main raw materials, including Class C, F or N. This is because most fly ashes contain appreciable amounts of disordered Al and Si, the basic elements of the geopolymer framework. However, this does not mean that the intrinsic reactivity of fly ash is not important for geopolymer production.

The reaction mechanism by which a geopolymer forms from a fly ash is very different from the mechanism by which a fly ash reacts with cementitious materials to form concrete or cement. This means that the measurements of fly ash reactivity for the cement industries are not appropriate for geopolymer production. This is because in the cement industries the reactivity measurements are developed based on the reaction between cement or calcium hydroxide and fly ash. Therefore approaches for measuring fly ash reactivity for use in concretes, such as conductivity, calcium consumption, hydration layer depth, gel surface area and volume, are unlikely to be appropriate.

Verification Experiments

Experiment 1: Assessing the Reactivity of Five Fly Ashes

Five fly ashes obtained from different power stations around Australia, denoted as A, B, C, D and E, were used as solid aluminosilicates for geopolymer synthesis. The bulk composition of these fly ashes, as determined by X-ray fluorescence (XRF), is shown in Table 1.

TABLE 1

Chemical Compositions of fly ash as measured by XRF, wt. %. LOI is loss of ignition at 1000° C.

| Fly ash | $SiO_2$ | $Al_2O_3$ | CaO | MgO | $K_2O$ | $Na_2O$ | $Fe_2O_3$ | $P_2O_5$ | $TiO_2$ | LOI |
|---|---|---|---|---|---|---|---|---|---|---|
| A | 47.5 | 27.3 | 4.25 | 1.48 | 0.54 | 0.74 | 14.3 | 0.91 | 1.47 | 0.53 |
| B | 53.3 | 32.5 | 6.90 | 0.90 | 0.59 | 0.27 | 3.10 | 0.10 | 1.60 | 0.50 |
| C | 54.4 | 32.1 | 1.06 | 0.75 | 0.22 | 0.14 | 7.49 | 0.09 | 2.14 | 0.85 |
| D | 67.3 | 22.5 | 1.00 | 0.53 | 2.11 | 0.50 | 3.74 | 0.09 | 0.90 | 0.90 |
| E | 71.2 | 24.7 | 0.08 | 0.12 | 0.53 | 0.01 | 1.16 | 0.04 | 1.42 | 0.43 |

According to ASTM C 618, these fly ashes can all be classified into Class F in terms of the total mass of $SiO_2$, $Al_2O_3$ and $Fe_2O_3$.

To examine the phases present in the five fly ashes, quantitative X-Ray Diffractometry (Q-XRD) was performed with Rietveld quantification analysis. All the powder samples, without any grinding or density classification, were mixed with 20% corundum (□-$Al_2O_3 \geq 99.99\%$, Aladdin) as internal standard. The XRD data were obtained on the ARL 9900 workstation (Bonvin et al. 2000) using Co radiation ($\lambda$=1.788996 nm), tube power of 40 KV and i=40 mA. The 2-theta degree was recorded from 8 to 80° with a step size of 0.02° and count time of 4 s/step. FIG. 1 shows the Q-XRD results, and the components are summarized in Table 2. In FIG. 1 the observed pattern is denoted by red crosses, the calculated pattern by the red solid upper line, and the difference between the patterns is illustrated by the bottom pink line. The dot marks denote the Bragg peaks of the different phases.

TABLE 2

Crystalline and amorphous phases of the five selected fly ashes as determined by Rietveld quantitative XRD method, wt. %.

| Components (ICSD) | A | B | C | D | E |
|---|---|---|---|---|---|
| Mullite, $Al_{4.75}Si_{1.25}O_{9.63}$ (66448) | 18.7 | | | 15.7 | 24.1 |
| Mullite, $Al_{1.83}Si_{1.08}O_{4.85}$ (43289) | | 13.6 | 15.3 | | |
| Quartz, $SiO_2$ (89280) | 3.1 | 2.6 | 6.5 | 5.0 | 13.1 |
| Magnetite, $Fe_3O_4$ (43001) | 2.5 | 1.3 | 2.4 | 0.9 | — |
| Hematite, $Fe_2O_3$ (15840) | 1.5 | 0.8 | — | — | — |
| Amorphous | 74.2 | 81.7 | 75.8 | 78.4 | 62.8 |
| $W_{RP}$, % | 3.02 | 6.05 | 3.89 | 3.32 | 5.03 |

Note:
composition of A and E is given as the average value obtained with three standard levels.

Next, the composition of the amorphous fraction was calculated based the bulk composition and the determined crystalline components (i.e. using the data illustrated in Tables 1 and 2). First, the crystalline phase compositions illustrated in Table 2 were converted to equivalent oxide compositions (in wt. %) so that they are comparable to the XRF results provided in Table 1. Secondly, the wt. % of these converted crystalline compositions were subtracted from the bulk compositions provided in Table 1. In this step, the LOI and trace elements were all subscribed to the composition in amorphous phase. The calculation result is given in Table 3. Table 3 therefore illustrates the amount (in wt. % of the total fly ash sample) of the components of the amorphous phase.

TABLE 3

Amorphous composition (wt. %) of fly ashes as calculated from the bulk composition and crystalline composition. 'Others' includes $P_2O_5$, $SO_3$, etc. trace composition and LOI.

| Fly ash | $SiO_2$ | $Al_2O_3$ | CaO | MgO | $K_2O$ | $Na_2O$ | $Fe_2O_3$ | $TiO_2$ | Others |
|---|---|---|---|---|---|---|---|---|---|
| A | 39.97 | 13.03 | 4.25 | 1.48 | 0.54 | 0.74 | 10.21 | 1.47 | 2.50 |
| B | 45.09 | 24.43 | 6.90 | 0.90 | 0.59 | 0.27 | 0.96 | 1.60 | 0.96 |
| C | 41.59 | 23.03 | 1.06 | 0.75 | 0.22 | 0.14 | 5.01 | 2.14 | 1.87 |
| D | 58.58 | 10.52 | 1.00 | 0.53 | 2.11 | 0.50 | 2.81 | 0.90 | 1.45 |
| E | 52.40 | 6.31 | 0.08 | 0.12 | 0.53 | 0.01 | 1.16 | 1.42 | 0.77 |

The measurement of particle surface area can be performed by a particle size analyzer or by Gas absorption via the Brunauer-Emmett-Teller (BET) method. In the results provided below, the surface area of the fly ashes was determined by a Malvern Mastersizer 2000 laser particle sizer. This equipment has a wide range measurement of materials, including emulsions, suspensions and dry powders. Particles of size from 0.02 μm to 2000 μm can be measured with an accuracy of ±1% on the $D_{50}$. Fly ash usually has a particle size range of <1-100 μm, which is suitable to be tested using this equipment.

The surface area (SA) can be calculated from the results of the particle size distribution measurement using the following equation:

$$SA = (6\Sigma(V_i/d_i))/(\rho\Sigma V_i) = 6/(\rho D[3,2])$$

in which: $V_i$ is the relative volume in class i with a mean class diameter of $d_i$, $\rho$ is the density of the material, and $D[3,2]$ is the surface area weighted mean diameter. This can be carried out automatically within the Malvern Mastersizer 2000 software, providing a means of rapidly estimating the particle surface area. In carrying out this calculation, it is assumed that the particles are perfectly solid spheres. It may be particularly suitable for the fly ash measurement since most of fly ash particles are spherical. If the particles are porous with open holes (like cenospheres) or irregular (such as milled ash), the calculation result is not accurate. BET method may give a more accurate result, but this method should consider the influence of residual carbon particles in fly ash. Before performing BET test it is recommended to exclude this influence by removing carbon particle through a water-oil flotation process (Hwang et al. 2002).

The surface area and particle parameters measured in for the fly ashes are summarized in Table 4.

TABLE 4

Particle characteristic parameters of fly ashes.

| Sample | A | B | C | D | E |
|---|---|---|---|---|---|
| Surface area/m²/g | 2.14 | 2.37 | 0.939 | 1.01 | 0.643 |
| $D_{10}$/μm | 0.97 | 1.00 | 2.91 | 2.14 | 5.34 |
| $D_{50}$/μm | 7.63 | 18.00 | 31.86 | 21.16 | 28.24 |
| $D_{90}$/μm | 42.14 | 64.50 | 141.05 | 65.65 | 66.34 |

The mass fraction of the amorphous phases was then converted into a molar ratio, as shown in Table 5.

TABLE 5

Amorphous composition of fly ashes in molar ratio

| Fly ash | $SiO_2$ | $Al_2O_3$ | CaO | MgO | $K_2O$ | $Na_2O$ | $Fe_2O_3$ | $TiO_2$ |
|---|---|---|---|---|---|---|---|---|
| A | 0.665 | 0.128 | 0.076 | 0.037 | 0.006 | 0.012 | 0.064 | 0.018 |
| B | 0.750 | 0.240 | 0.123 | 0.022 | 0.006 | 0.004 | 0.006 | 0.020 |
| C | 0.692 | 0.226 | 0.019 | 0.019 | 0.002 | 0.002 | 0.031 | 0.027 |
| D | 0.975 | 0.103 | 0.018 | 0.013 | 0.022 | 0.008 | 0.018 | 0.011 |
| E | 0.872 | 0.062 | 0.001 | 0.003 | 0.006 | 0.000 | 0.007 | 0.018 |

The $^{[5]}Fe$ and the distribution of $Fe^{2+}$ and $Fe^{3+}$ can be measured experimentally, or can be roughly estimated after considering the analysis results by Weigel et al. (2008). Analyzing the $NaFe_xAl_{1-x}Si_2O_6$ (x=1, 0.8, 0.5) indicates that $Fe^{3+}/Fe$ decreased from 88% to 86% and $^{[5]}Fe$ decreased from 36 to 32% as x decreased from 1 to 0.5 (Weigel et al. 2008). Using a simple linear regression (as illustrated in the equations provided above), the $Fe^{3+}/Fe$ and $^{[5]}Fe$ can be estimated to be 44% to 87%, and 51% to 83% respectively. The calculations for the concentration of reactive bonds (C, as discussed above) of each of the fly ashes is provided in Table 6.

TABLE 6

Concentration of reactive bonds (molar ratio) in each of the five fly ashes

| Fly ash | Si | Ti | Al | 2Ca + 2Mg + Na + K | Fe | $Fe^{3+}$ | $^{[5]}Fe$ | 2 $^{[5]}Fe^{2+}$ + 3 $^{[5]}Fe^{3+}$ | Reactive Bonds |
|---|---|---|---|---|---|---|---|---|---|
| A | 0.665 | 0.018 | 0.256 | 0.260 | 0.128 | 0.110 | 0.515 | 0.188 | 0.449 |
| B | 0.750 | 0.020 | 0.479 | 0.312 | 0.012 | 0.005 | 0.541 | 0.016 | 0.328 |
| C | 0.692 | 0.027 | 0.452 | 0.084 | 0.063 | 0.055 | 0.821 | 0.148 | 0.232 |
| D | 0.975 | 0.011 | 0.206 | 0.123 | 0.035 | 0.029 | 0.616 | 0.061 | 0.184 |
| E | 0.872 | 0.018 | 0.124 | 0.020 | 0.015 | 0.013 | 0.830 | 0.035 | 0.055 |

The concentration of reactive bonds may then be multiplied with the surface area of the fly ash to provide a Reactivity Index (RI), as shown in Table 7. The estimated Reactivity Index (RI) is between 0.035 and 0.961 m²/g, and the RI from high to low is in the order of A>B>C>D>E.

TABLE 7

Estimated Reactivity Index (RI) of the five fly ashes

| Fly ash | Reactive Bonds | SA (m²/g) | RI (m²/g) |
|---|---|---|---|
| A | 0.449 | 2.14 | 0.961 |
| B | 0.328 | 2.36 | 0.774 |
| C | 0.232 | 0.939 | 0.218 |
| D | 0.184 | 1.01 | 0.186 |
| E | 0.055 | 0.643 | 0.035 |

To verify this index, the five fly ashes were activated with the same sodium hydroxide and sodium silicate mix solution. The activator solution was mixed with fly ash for 5 min and then additional water, if needed, was added and mixed for 2-3 min until a uniform paste was obtained. Table 8 provides the composition of the binder mixture, and also indicates the adjusted concentration of dissolved Si, $Na^+$ and $OH^-$ because of utilization of additional water.

TABLE 8

Composition of geopolymer mixtures and concentration of Si, Na+ and OH−

| Fly Ash | Fly Ash (g) | NaOH/Na$_2$SiO$_3$ Activator solution (g) | Additional Water (g) | Liquid/Ash (g/g) | Adjusted Concentration Si (mol/L) | Na+ (mol/L) | OH− (mol/L) |
|---|---|---|---|---|---|---|---|
| A | 1000 | 395 | 0 | 0.395 | 4.3 | 8.8 | 4.6 |
| B | 1000 | 395 | 158 | 0.553 | 3.1 | 6.6 | 3.4 |
| C | 1000 | 395 | 50 | 0.445 | 3.4 | 7.0 | 3.7 |
| D | 1000 | 395 | 100 | 0.495 | 3.0 | 6.7 | 3.5 |
| E | 1000 | 395 | 255 | 0.650 | 2.5 | 5.1 | 2.7 |

Figure 2:
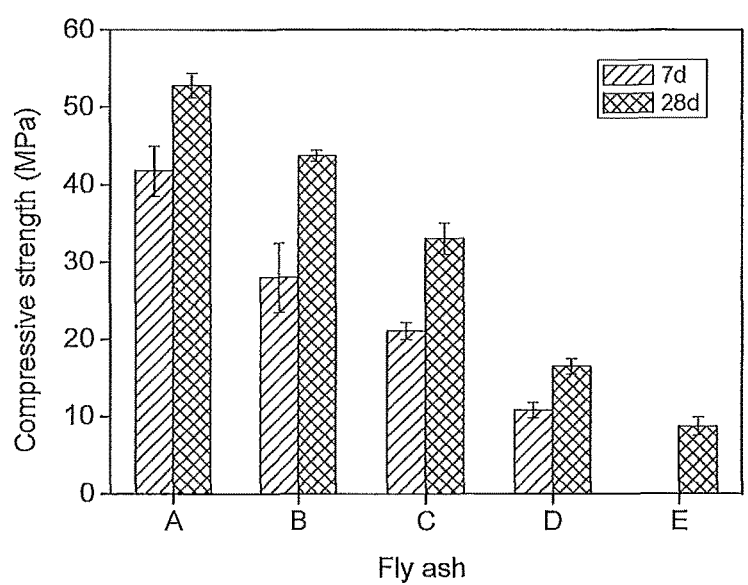
FIG. 2 shows the compressive strength of hardened geopolymer pastes at 7 days and 28 days.

The paste was cast in Ø50×100 mm plastic molds and was cured at 40° C. for first 24 h, followed by hardening at ambient condition. The compressive strengths of hardened pastes at 7 days and 28 days were tested, and this is shown in FIG. 2. Fly ash A exhibited the highest compressive strength (41.8 MPa at 7 d and 52.8 MPa at 28 d). For the geopolymer synthesised from fly ash E, however, the compressive strength was too low to be tested (<1 MPa) at 7 d, but after 28 d an average compressive strength of 8.7 MPa was achieved.

Figure 3:
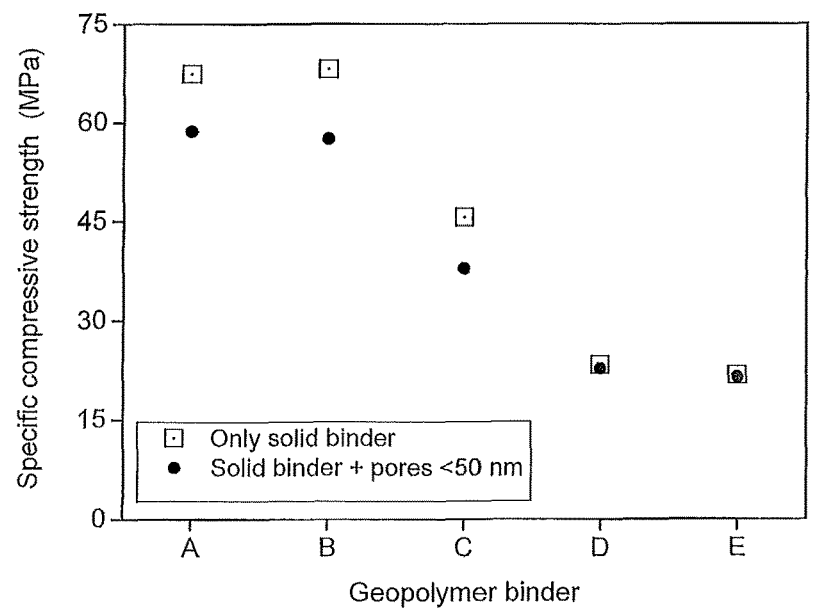
FIG. 3 shows the specific compressive strengths of 28-day hardened geopolymer pastes.

The strength of the different geopolymers made may be affected by the porosity of the different fly ashes. The specific strength of the hardened pastes were calculated by measurement of the pore size distribution and the porosity of the hardened paste by mercury intrusion porosimetry. To exclude the effects of pores, two specific compressive strengths at 28 days were considered. One is the ratio of compressive strength to volume fraction of solid binder (i.e. 1-porosity), while the other is defined as the ratio of compressive strength to volume fraction of solid binder and pores <50 nm, supposing that the pores <50 nm do not affect mechanical strength (see FIG. 3). When the small pores are taken into consideration, fly ash A (i.e. binder A in FIG. 3) exhibits the highest strength. In combination with the 'apparent' compressive strength, there is no close relationship between compressive strength and porosity or pore size distribution. The mechanical testing result generally fits with the order of RI of the fly ashes.

To address the possibility that the additional water used in mixtures B, C, D and E changed the activation conditions, a second set of experiments was conducted in which activation of fly ashes A, B and E was conducted with an activator at a lower concentration. Table 9 lists the composition of the geopolymer mixtures. It should be noted that the water was premixed with the activator instead of being added directly to the pastes. The low concentration activator was prepared and cooled down at least 24 h prior to use.

TABLE 9

Composition of geopolymer mixtures activated with lower concentration solution

| Fly Ash | Fly Ash (g) | NaOH/Na$_2$SiO$_3$ Activator solution (g) | Additional Water (g) | Liquid/Ash (g/g) | Adjusted Concentration Si (mol/L) | Na+ (mol/L) | OH− (mol/L) |
|---|---|---|---|---|---|---|---|
| A | 1000 | 280 | 70 | 0.350 | 3.4 | 7.0 | 3.7 |
| B | 1000 | 359 | 91 | 0.450 | 3.4 | 7.0 | 3.7 |
| E | 1000 | 479 | 121 | 0.600 | 3.4 | 7.0 | 3.7 |

Figure 4:
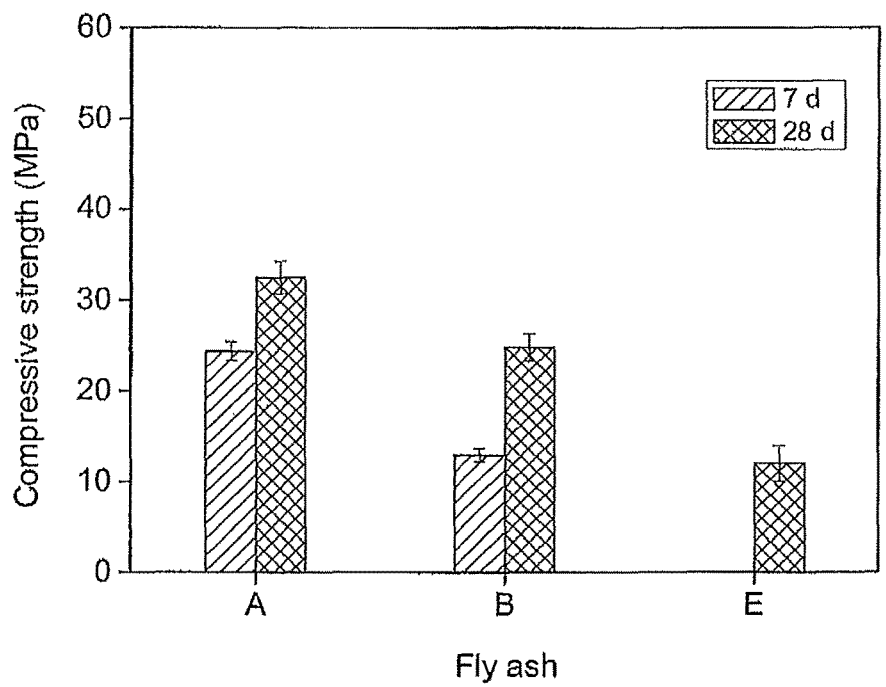
FIG. 4 shows the compressive strength of geopolymers synthesised with low concentration activator solution at 7 days and 28 days.

The compressive strength was tested after the same curing and aging procedure as above, and the results are shown in FIG. 4. As expected, the resultant geopolymer specimens exhibited an order of compressive strength of A>B>E.

Experiment 2: Comparison with Work by Rickard et al. (2011)

In Rickard et al. (2011) the composition of three fly ash samples was provided (as shown in Table 10), along with their surface area (in m$^2$/cm$^3$), density and compressive strength. This data may be used to calculate a reactivity index for these fly ashes, as described above.

TABLE 10

Chemical Composition of three fly ashes

| Amorphous oxide (wt %) | Collie | Eraring | Tarong |
|---|---|---|---|
| SiO$_2$ | 20.9 | 45.09 | 42.79 |
| Al$_2$O$_3$ | 15.39 | 7.67 | 4.11 |
| Fe$_2$O$_3$ | 9.11 | 2.49 | 0.64 |
| CaO | 1.74 | 1.59 | 0.08 |
| K$_2$O | 0.9 | 1.68 | 0.53 |
| TiO$_2$ | 1.47 | 0.84 | 1.28 |
| MgO | 1.41 | 0.51 | 0.17 |
| Na$_2$O | 0.41 | 0.56 | 0.09 |
| P$_2$O$_5$ | 1.09 | 0.27 | 0.08 |

This data can be used to provide the amorphous composition of fly ashes in molar ratio, as shown in Table 11.

TABLE 11

Amorphous composition of fly ashes in molar ratio

| Amorphous Oxide | Collie | Eraring | Tarong |
|---|---|---|---|
| Fe$_2$O$_3$ | 0.057 | 0.016 | 0.0040 |
| CaO | 0.031 | 0.028 | 0.0014 |
| K$_2$O | 0.0096 | 0.018 | 0.0056 |
| MgO | 0.035 | 0.013 | 0.0042 |
| Na$_2$O | 0.0066 | 0.0090 | 0.0015 |
| Reactive bonds | 0.28 | 0.17 | 0.034 |

The surface area (in m$^2$/g) may also be calculated from the measured surface area (in m$^2$/cm$^3$) and density (g/cm$^3$), as shown in Table 12.

TABLE 12

Surface Area Calculation

| | Collie | Eraring | Tarong |
|---|---|---|---|
| Surface area (in m$^2$/cm$^3$) | 1.59 | 0.92 | 0.99 |
| Density (g/cm$^3$) | 2.4 | 2.02 | 2 |
| SA in mass (in m$^2$/g) | 0.66 | 0.46 | 0.50 |

The reactivity of each fly ash may then be calculated by multiplying the surface area by the reactive bonds, as shown in Table 13.

TABLE 13

Reactivity index calculation for each fly ash, compared to the measured compressive strength

| Amorphous Oxide | Collie | Eraring | Tarong |
|---|---|---|---|
| SA in mass (in m$^2$/g) | 0.66 | 0.46 | 0.50 |
| Reactive bonds | 0.28 | 0.17 | 0.033 |

TABLE 13-continued

Reactivity index calculation for each fly ash,
compared to the measured compressive strength

| Amorphous Oxide | Collie | Eraring | Tarong |
|---|---|---|---|
| Reactivity index (RI) | 0.18 | 0.076 | 0.017 |
| 28 day compressive strength (MPa) | 53 | 33 | 26 |

As illustrated in Table 13, the calculated reactivity corresponds well with the measured compressive strength.

In compliance with the statute, the invention has been described in language more or less specific to structural or methodical features. It is to be understood that the invention is not limited to specific features shown or described since the means herein described includes preferred forms of putting the invention into effect. The invention is, therefore, claimed in any of its forms or modifications within the proper scope of the appended claims appropriately interpreted by those skilled in the art.

CONCLUSIONS/SUMMARY

Therefore, by using the methods of the present invention an operator is able to determine the reactivity of an polymerizable material in forming a geopolymer. Advantageously:

The methods allow an operator to determine the reactivity of the polymerizable material based on the chemical composition of the polymerizable material alone. This can take significantly less time than prior art methods, such as US201105291;

Using the methods of the present invention an operator is able to determine the reactivity of the polymerizable material, independent of other variables such as the molarity and agents used in the alkaline polymerization reaction, the temperature of the polymerization reaction, and the water-to-solid ratio of the polymerization reaction;

Using the methods of the present invention an operator is able to assess whether supposedly less reactive polymerizable material (such as Class F fly ashes) would be effective for geopolymer production;

If the present invention allows a greater range of polymerizable material to be used for geopolymer production, then this may reduce the quantity of polymerizable material being disposed of in landfills and/or lagoons;

Using the methods of the present invention a geopolymer manufacturer can reduce the alkaline activator usage, i.e. optimize the quantity of alkali metal or alkaline earth hydroxide or silicate according to the chemical nature of each particular polymerizable material;

The present invention provides information about the role of alkaline and alkali earth cations, and the role of iron and other cations in forming a geopolymer. This is helpful in understanding the leaching properties of the geopolymer and the durability as well; and The present invention provides information about the manufacturing of light weight geopolymer concrete using pre-foaming methods, chemical foaming methods and using lightening aggregate methods. This is aimed at the development of thermal insulation and fire resistant geopolymer concretes.

CITATION LIST

Bakharev, T., 2005. Geopolymeric materials prepared using Class F fly ash and elevated temperature curing. Cement and Concrete Research, 35, pp. 1224-1232.

Bonvin, D., Yellepeddi, R. & Buman, A., 2000. Application and perspectives of a new innovative XRF-XRD spectrometer in industrial process control. JCPDS-International Centre for Diffraction Data 2000, Advances in X-ray Analysis, 42, pp. 126-136.

Bumrongjaroen, W., Muller, I. S., et al., 2007. Characterization of Glassy Phase in Fly Ash From Iowa State University. (Technical Report) Used in Development of Performance Properties of Ternary Mixes: Transportation Pooled Fund Program of USDOT/FHWA, VSL-07R520

Criado, M., Palomo, A. & Fernandez-Jimenez, A., 2005 Alkali activation of fly ashes. Part 1: Effect of curing conditions on the carbonation of the reaction products. Fuel, 84(16), pp. 2048-2054.

Diaz-Loya, E. I., Allouche, E. N. & Vaidya, S., 2011. Mechanical Properties of Fly-Ash-Based Geopolymer Concrete. ACI Materials Journal, 108(3), pp. 300-306.

Dombrowski, K. & Buchwald, A., 2007. The influence of calcium content on the structure and thermal performance of fly ash based geopolymers. Journal of materials science, 42, pp. 3033-3043.

Hwang, J. Y., Sun, X. & Li, Z., 2002. Residual carbon in fly ash for mercury adsorption: I. Separation and characterization of unburned carbon. Journal of Minerals & Materials Characterization & Engineering, 1(1), pp. 39-60.

Keyte, L., 2008. What's wrong with Tarong? The importance of coal fly ash glass chemistry in inorganic polymer synthesis, Doctor of Philosophy thesis, The University of Melbourne, Australia. 2008. The University of Melbourne.

Mysen, B. O. & Virgo, D., 1985. Iron-bearing silicate melts: Relations between pressure and redox equilibria. Physics and Chemistry of Minerals, 12(4), pp. 191-200.

Rickard, W. D. a. et al., 2011. Assessing the suitability of three Australian fly ashes as an aluminosilicate source for geopolymers in high temperature applications. Materials Science and Engineering: A, 528(9), pp. 3390-3397.

Provis, J. et al., 2009. Valorasation of fly ashes by geopolymerisation. Global NEST Journal, 11(2), pp. 147-154.

Weigel, C. et al., 2008. Intermediate-range order in the silicate network glasses $NaFe_xAl_{1-x}Si_2O_6$ (x=0,0.5,0.8,1): A neutron diffraction and empirical potential structure refinement modeling investigation. Phys. Rev. B, 78, pp. 064202-064212.

The invention claimed is:

1. A method of assessing the reactivity of a polymerizable material in forming a geopolymer, the method comprising:
   assessing whether the polymerizable material is layered or particulate; and
   if the polymerizable material is layered, measuring the moles of polymerization network forming elements in an amount of polymerizable material, whereby the moles of polymerization network forming elements is indicative of the reactivity of the polymerizable material in forming a geopolymer; or
   if the polymerizable material is particulate, measuring the molar charge of polymerization network modifiers in an amount of polymerizable material, whereby the molar charge of polymerization network modifiers is indicative of the reactivity of the polymerizable material in forming a geopolymer.

2. The method of claim 1, further including the step of measuring the chemical composition of the polymerizable material.

3. The method of claim 1, wherein the reactivity of the polymerizable material in forming a geopolymer increases as the moles of polymerization network forming elements increases, or as the molar charge of polymerization network modifiers increases.

4. The method of claim 1, further including the step of determining the surface area of the polymerizable material, whereby the reactivity of the polymerizable material in forming a geopolymer increases as the surface area increases.

5. The method of claim 1, wherein the polymerizable material is layered, and the layered polymerizable material is a heated clay.

6. The method of claim 5, wherein the polymerization network forming elements include one or more of silicon, aluminium and phosphorous.

7. The method of claim 5, wherein the polymerization network forming elements are in the amorphous phase of the polymerizable material.

8. The method of claim 1, wherein the polymerizable material is particulate, and the particulate polymerizable material is selected from silica fume, superfine silica powder, slag, fly ash, combustion ash, treated reservoir sludge, waste and prepared aluminosilicate and non-iron and iron-bearing glasses.

9. The method of claim 8, wherein the particulate polymerizable material is fly ash.

10. The method of claim 8, wherein the polymerization network modifiers are compounds of alkali metal and alkaline earth elements.

11. The method of claim 8, wherein the polymerization network modifiers are in the amorphous phase of the polymerizable material.

12. The method of claim 8, wherein the method includes the further step of determining the molar charge of polymerization network modifying iron in the amount of particulate polymerizable material, whereby the molar charge of polymerization network modifying iron is indicative of the reactivity of the polymerizable material in forming a geopolymer.

13. The method of claim 12, wherein the molar charge of polymerization network modifying iron in the amount of polymerizable material is the molar charge of 5-coordinated $Fe^{3+}$ and $Fe^{2+}$.

14. The method of claim 1, wherein as the reactivity of the polymerizable material increases, then the geopolymer formed from the polymerizable material is predicted to possess one or more of: increased compressive strength, increased flexural strength, increased bending strength, increased tension strength and increased compression modulus.

15. A method of forming a geopolymer, the method comprising:
providing a polymerizable material;
assessing the reactivity of the polymerizable material by the method of claim 1; and
polymerising the polymerizable material to form a geopolymer.

16. The method of claim 15, further including the step of milling the polymerizable material prior to the step of assessing the reactivity of the polymerizable material.

17. The method of claim 15 further including providing the formed geopolymer.

18. A method of assessing the reactivity of a particulate polymerizable material in forming a geopolymer, the method comprising:
determining moles of polymerization network modifier compounds in an amount of particulate polymerizable material,
whereby the moles of polymerization network modifier compounds is indicative of the reactivity of the particulate polymerizable material in forming a geopolymer.

19. The method of claim 1, wherein the polymerizable material is layered and the method includes the steps:
measuring the surface area of the polymerizable material; and
calculating the reactivity of the polymerizable material in forming a geopolymer by multiplying the surface area of the polymerizable material by the moles of polymerization network forming elements in the polymerizable material.

20. The method of claim 1, wherein the polymerizable material is particulate and the method includes the steps:
measuring the molar charge of polymerization network modifying iron in the amount of polymerizable material, and the surface area of the polymerizable material; and
calculating the reactivity of the polymerizable material in forming a geopolymer by multiplying the surface area of the polymerizable material by the sum of the molar charge of polymerization network modifiers and the molar charge of polymerization network modifying iron in the polymerizable material.

* * * * *